United States Patent [19]

Guggenbühl

[11] 4,277,743
[45] Jul. 7, 1981

[54] METHOD AND CIRCUIT FOR PRODUCING MEASURING PULSES IN A PARTICLE ANALYZER

[75] Inventor: Walter Guggenbühl, Stäfa, Switzerland

[73] Assignee: Contraves AG, Zürich, Switzerland

[21] Appl. No.: 923,915

[22] Filed: Jul. 12, 1978

[30] Foreign Application Priority Data

Aug. 25, 1977 [CH] Switzerland .................. 10390/77

[51] Int. Cl.³ .............................................. G01N 27/00
[52] U.S. Cl. .................................................. 324/71 CP
[58] Field of Search .................. 324/71 CP, 64, 71 R; 235/92 PC; 364/55

[56] References Cited

U.S. PATENT DOCUMENTS

| | | |
|---|---|---|
| 3,706,030 | 12/1972 | Klein et al. |
| 3,924,180 | 12/1975 | Salzman et al. .................. 324/71 CP |
| 3,993,948 | 11/1976 | Epstein . |
| 4,093,849 | 6/1978 | Baxter et al. ..................... 235/92 PC |

FOREIGN PATENT DOCUMENTS

| | | |
|---|---|---|
| 2057274 | 8/1969 | France . |
| 546437 | 2/1974 | Switzerland . |
| 391797 | 5/1933 | United Kingdom . |
| 927346 | 5/1963 | United Kingdom . |
| 968491 | 9/1964 | United Kingdom . |
| 976622 | 12/1964 | United Kingdom . |
| 980206 | 1/1965 | United Kingdom . |
| 1061776 | 3/1967 | United Kingdom . |
| 1093461 | 12/1967 | United Kingdom . |
| 1129162 | 10/1968 | United Kingdom . |
| 1336503 | 11/1973 | United Kingdom . |

Primary Examiner—Michael J. Tokar
Attorney, Agent, or Firm—Werner W. Kleeman

[57] ABSTRACT

A method of, and circuit for, producing measuring pulses in a particle analyzer for the analysis of particles suspended in a liquid, especially blood cells, comprising a conductivity or measuring cell, whose impedance between two terminals of the conductivity cell changes upon passage of a particle through such conductivity cell. A controllable current supply powers the conductivity cell with a current regulated to maintain a reference value corresponding to a control value. A receiver functioning as a high-pass filter and having high input impedance serves for the essentially currentless removal of a potential between the terminals of the conductivity cell and for forming a receiver signal corresponding to such components of such potential whose frequency is above a threshold or cut-off frequency corresponding to the high-pass filter. The control value is formed from the sum of a predetermined reference value and the received signal. There is formed a measuring signal proportional to the difference of the control value and the reference value and whose timewise changes correspond to the measuring pulses.

7 Claims, 2 Drawing Figures

METHOD AND CIRCUIT FOR PRODUCING MEASURING PULSES IN A PARTICLE ANALYZER

BACKGROUND OF THE INVENTION

The present invention relates to a new and improved method of, and circuit for, generating measuring pulses in a particle analyzer for the analysis of particles suspended in a liquid, especially for the analysis of blood cells.

The equipment of the present development is generally of the type comprising a conductivity or measuring cell, the impedance of which between two terminals of the conductivity cell changes upon passage of a particle through the conductivity cell. Further, there is provided a controllable current supply for supplying the conductivity cell with a current which is regulated for maintaining a reference value corresponding to a control value. A receiver acting as a high-pass filter and having high input impedance serves for the essentially currentless removal of a potential or voltage between the terminals of the conductivity cell and for the formation of a receiver signal which corresponds to such components of such potential whose frequency lies above a threshold or cut-off frequency corresponding to the high-pass filter.

As already mentioned the invention relates to circuitry for producing measuring pulses in a particle analyzer for the analysis of particles suspended in a liquid, especially particles in the form of blood cells, and which apparatus comprises a conductivity or measuring cell having at least two terminals, between which there can be measured a change in impedance upon passage of a particle through the conductivity cell. There is also provided a controllable current supply having a control input and two output terminals, wherein each respective one is connected with a respective terminal of the conductivity cell. There is also provided a receiver composed of a combination of an amplifier having high input impedance and a high-pass filter having an appropriate threshold or cut-off frequency.

Now from Swiss Pat. No. 420,669 there is known to the art, by way of example, a current source which delivers a constant direct-current and a receiver whose input impedance for direct-current is extremely high and, on the other hand, is extremely low for alternating-current or pulses above a predetermined threshold or cut-off frequency. If with such type equipment a particle passes through the conductivity cell, then there is produced in the conductivity cell a pulse-like change of the impedance, whereupon there is branched-off from the conductivity cell an appropriate part of the current delivered by the current source and delivered to the receiver. In the receiver the branched-off current part is detected as a measuring pulse. The volume of the particles which are to be analyzed is proportional to the relative change of the impedance of the conductivity cell during passage of a particle. However, with this equipment the measuring pulse is only approximately proportional to the relative change of the impedance of the conductivity cell, since the proportionality is only valid to the extent that the branched-off current part remains negligibly small in comparison to the total current delivered by the current source. In order to fulfill this condition a rather high current must flow through the conductivity cell. This, in turn, causes disadvantageous electrochemical and thermal side effects, for instance a polarization of the electrodes of the conductivity cell, formation of bubbles at the electrodes, heating-up of the liquid, and a delay in maintaining the equilibrium state of the conductivity cell after placing the equipment into operation.

Also it is known, for instance, from Swiss Pat. No. 546,437 to maintain small enough yet constant the current flowing through the conductivity cell and at the same time to insure for the desired proportionality of a measuring pulse with regard to the relative change of the impedance of the conductivity cell. For this purpose the receiver is designed to have a high input impedance. At the terminals of the conductivity cell there are measured voltage pulses, and the direct-current voltage applied to the conductivity cell, i.e., the quiescent value of the voltage is maintained constant with the conductivity cell free of particles. With constant current the quiescent or static voltage is markedly dependent upon the temperature of the liquid, so that there is contemplated a control of the current source in order to maintain constant the quiescent voltage without causing disappearance of the voltage pulses to be measured. For this purpose the control of the current source has a time-constant, so that it only responds to such voltage changes whose frequency spectrum is below a predetermined threshold frequency. It is assumed that the temperature-dependent changes of the impedance of the conductivity cell take place much more slowly than the changes of such impedance which are brought about during through-passage of a particle. What is disadvantageous with this solution is that the quiescent current flowing through the conductivity cell free of particles only can be influenced by means of the value of a reference potential or voltage which controls the control device or control. The current is intentionally maintained temperature-dependent, however the desired and therefore strived for result is not achieved, because the current-voltage characteristic of the measuring cell is not linear. Furthermore, during the course of the same working day it can happen that the quiescent current periodically is optimum, but however periodically is too small or too great.

Now in the same Swiss Pat. No. 546,437 it is proposed to supply the conductivity cell which is connected in series with a choke by means of a constant voltage source. Since the voltage source has low internal resistance, it will be apparent that the potential between the terminals of the conductivity cell remains approximately constant during slow changes in the impedance of the conductivity cell, whereas during pulse-like changes of this impedance there can be removed a voltage pulse at the terminals of the conductivity cell. With this solution the quiescent current in the particle free-conductivity cell can be directly adjusted by means of the voltage. However, such circuit is unstable in terms of the temperature, since temperature fluctuations cause corresponding uncontrollable current changes which can lead even to self-destruction of the circuit.

SUMMARY OF THE INVENTION

Hence, with the foregoing in mind it is a primary object of the present invention to provide a new and improved method of, and circuit for, producing measuring pulses in a particle analyzer which is not associated with the aforementioned drawbacks and limitations of the prior art proposals.

Another and more specific object of the present invention aims at providing a new and improved method of and circuit for particle analysis of the previously mentioned character, by means of which there can be avoided the above-indicated drawbacks, and in particular wherein the current flowing through the conductivity cell is constant, but can be selected as an independent parameter and thereby optimized, and the peak of the measuring pulses is independent of the temperature of the liquid.

Now in order to implement these and still further objects of the invention, which will become more readily apparent as the description proceeds, the method aspects of the present invention are manifested by the features that the control value is formed of the sum of a predetermined reference value and the receiver signal. There is formed a measuring signal proportional to the difference of the control value and the reference value, wherein changes as a function of time of the measuring signal constitute the measuring pulses. In practising the method it is preferable to form an actual value which is essentially the same as the control value, and the measuring signal is formed from the difference of the actual value and the reference value.

Not only is the invention concerned with the aforementioned method aspects, but also relates to circuit for the performance thereof, which is manifested by the features that the current supply constitutes a series circuit of a constant supply voltage source, a resistor or resistance and a current-determining element controllable by means of the control input. There is also provided a difference forming-computation network or unit, at the output of which there appear the measuring pulses and as concerns the inputs thereof one of such inputs is connected with a reference voltage source as well as by means of a low-pass filter with an output of the receiver.

According to a first preferred constructional embodiment of the circuit the other non-inverting input of the computation network and the control input is connected with the output of the receiver. In accordance with another preferred construction of the inventive circuit there is provided a differential amplifier whose output is connected with the control input and as to its inputs the one non-inverting input is connected with the output of the receiver, whereas the other inverting input of the differential amplifier is connected with the other non-inverting input of the computation network as well as with a terminal which is common to the resistor and the element, and the other terminal of the resistor is connected to the supply voltage source.

Preferably the current-determining element is a semiconductor element operated in the saturation region and having a control input for a voltage governing the value of the current.

In this manner and with these means there is achieved the beneficial result that the current supply counteracts such changes of the impedance of the conductivity cell whose frequency spectrum is below the cut-off or threshold frequency, in a manner such that there can be maintained constant the current flowing through the measuring cell. Furthermore, the current supply simultaneously counteracts such changes of the impedance of the measuring cell whose frequency spectrum is located above the cut-off frequency, in such a manner that there can be maintained constant the voltage applied to the conductivity cell. The current flowing through the conductivity cell is essentially determined by the voltage of both voltage sources and by the constant resistor. It is therefore directly adjustable and can be relatively small. The pulse peak at the output of the circuit is independent of the temperature of the liquid in the conductivity cell, because the pulses, as calculations have shown, are proportional to the current which is maintained constant, the aforementioned resistor and the relative impedance changes in the conductivity cell triggered by the particles. Additionally, the pulse peak, in comparison to the pulse peak obtained with the state-of-the-art circuits, is increased by the ratio of the resistance to the impedance of the conductivity cell. Finally, by virtue of the different mode of operation of the control of the current supply, depending upon the frequency range, it is possible to attain the equilibrium state of the entire device much more quickly following the turning-on of the current supply than is possible with the conventional current or voltage controlled supplies. These and further advantages, especially the simple construction of the circuit, will become more readily evident from the description and explanations given hereinafter.

BRIEF DESCRIPTION OF THE DRAWINGS

The invention will be better understood and objects other than those set forth above, will become apparent when consideration is given to the following detailed description thereof. Such description makes reference to the annexed drawings wherein throughout the various embodiments there have been generally used the same reference characters for the same or analogous components and wherein.

DETAILED DESCRIPTION OF THE PREFERRED EMBODIMENTS

Figure 1:
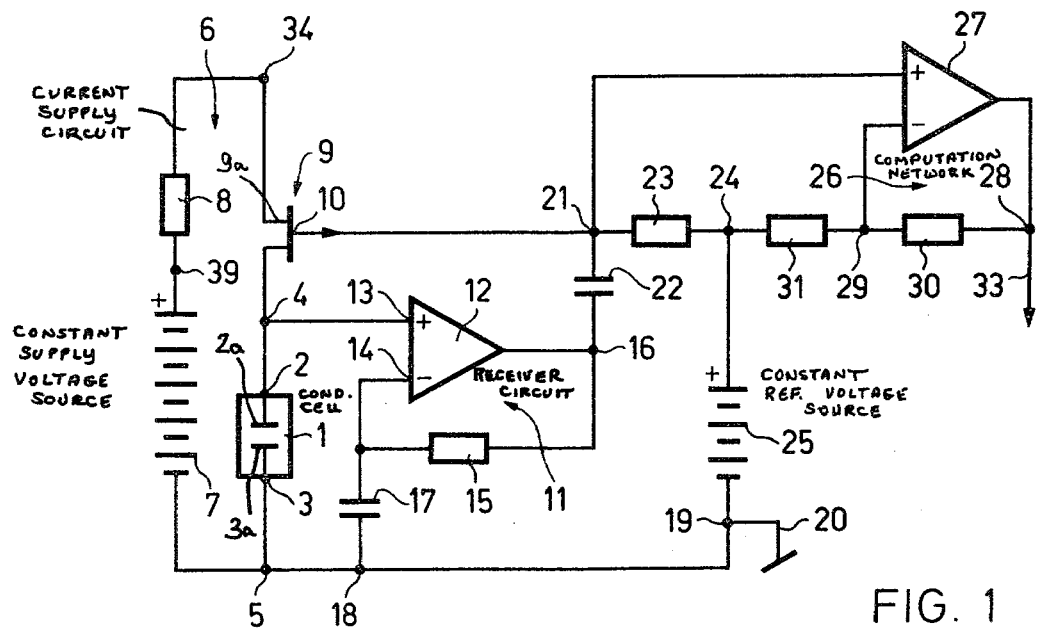
FIG. 1 is a circuit diagram of a first embodiment of particle analyzer.
Figure 2:
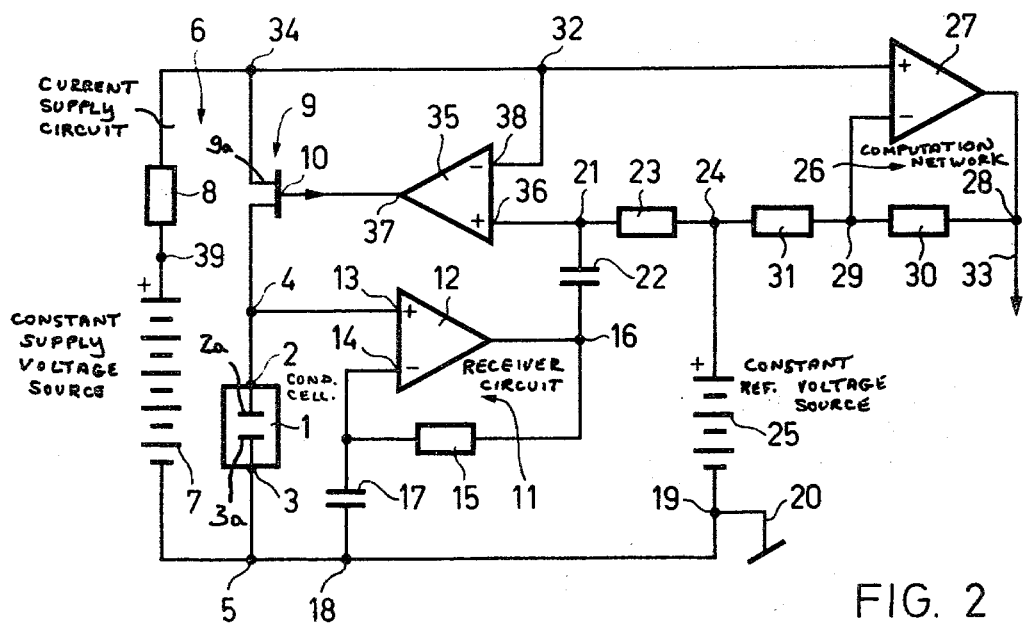
FIG. 2 is a circuit diagram of another preferred construction of particle analyzer.

Describing now the drawings, in both FIGS. 1 and 2 there has been illustrated a conductivity or measuring cell 1 for a particle analyzer. As is well known in this particular field of technology, such conductivity cell 1 consists of two vessels separated by an electrically insulating wall and containing a suspension of particles in a liquid and which are to be analyzed, a channel penetrating through the wall and two electrodes 2a and 3a, each electrode being in one of the vessels and contacting the liquid. The electrodes 2a, 3a are connected with the terminals 2 and 3 of the conductivity cell. Owing to a suitable pressure differential between both of the vessels the suspension is conveyed through the channel. Due to the different properties of the liquid and the particles an impedance of the conductivity cell 1 which can be measured between the terminals 2 and 3 becomes greater in a pulse-like manner when a particle is momentarily located in the channel. The impedance of the particle free channel essentially governs the quiescent value $R_k$ of the impedance of the measuring cell 1. The change in the impedance of the measuring cell 1 owing to the particle throughpassage has been conveniently designated by reference character $dR_k$.

Connected in circuit between and with the two terminals 4 and 5 is a controllable current supply. This current supply has been generally designated in its entirety by reference character 6. It consists of a constant supply voltage source 7, a resistor or resistance 8 and a current determining element 9 which is provided with a control input 10. In the illustrated construction the current determining element 9 constitutes a field-effect transistor which is operated in the saturation region. However, there can be employed other semiconductor elements having a saturation region, for instance a bipolar transistor or also an opto-coupler which is switched in suitable manner. The current circuit encompassing the measuring cell 1 and the current supply 6 consists of the series circuit of the supply voltage source 7 and the resistor 8 between the terminal 5 and a line node or junction 34, followed by the internal resistance of the field-effect transistor 9 between the line node 34 and the terminal 4, followed by the measuring cell 1 between the terminals 4 and 5, so that the current circuit is closed. At the line node or junction 34 there is connected the infeed terminal 9a of the field-effect transistor 9, thereby insuring that between the line node 34 and the control input 10 there prevails a constant voltage difference. The principle of this circuit is known as a series current-negative feedback, and the employment of another semiconductor element than the described field-effect transistor likewise could be accomplished in such circuit, something which would be readily apparent to one skilled in the electronics art and therefore need not here be further described. Finally, it is apparent that the line node 34 constitutes a common terminal for both of the resistances 8 and 9, and that the other terminal 39 of the constant resistor 8 is connected with the supply voltage source 7.

A receiver generally designated by reference character 11 contains an operational amplifier 12 having high input impedance. An input terminal 13 of a non-inverting input of the operational amplifier 12 is connected with the terminals 4 and 2, and thus, with the one electrode 2a of the measuring cell 1. Another input terminal 14 of an inverting input of the operational amplifier 12 is connected by means of a resistor 15 with an output terminal 16 of the operational amplifier 12 and by means of a capacitor 17 as well as a line node or junction 18 with the terminal 5 and thus with the other electrode 3a of the measuring cell 1. Additionally, the line node 18 is connected by means of another line node 19 with the ground conductor or ground 20. Such type circuit functions, as is known, as a high-pass filter for the voltage or potential which is tapped-off at the measuring cell 1 between the terminals 2 and 3. The threshold or cut-off frequency of the high-pass filter corresponds to the time-constant of the series circuit of the resistor 15 and the capacitor 17. The output terminal 16 of the operational amplifier 12 is connected with an output or an output terminal 21 of the receiver 11 by means of a capacitor 22, whereas the output terminal 21 is connected by means of a resistor 23, a line node 24 and an extremely low internal impedance of a constant reference voltage source 25, the function of which will be explained more fully hereinafter. Additionally, both the resistors 15 and 23 and both the capacitors 17 and 22 are identical, so that the series circuit of the capacitor 22 and the resistor 23 forms a second high-pass filter of the same threshold or cut-off frequency. It can be easily computated that the phase shift of both high-pass filters is essentially compensated to 90°, so that a signal appears at the output 21 of the receiver 11 which is proportional to the first time derivative of such voltage changes between the terminals 2 and 3 of the conductivity or measuring cell 1, the frequency spectrum of which is above the threshold or cut-off frequency, and the constant voltage of the reference voltage source 25 is superimposed upon the signal at the output 21 of the receiver 11.

A computation or arithmetic network, generally designated in its entirety by reference character 26, measures this signal at the output 21 of the receiver 11 in that it subtracts from this signal the voltage of the reference voltage source 25. For this purpose, the computation network 26 is constructed as a difference forming-computation network of known construction. It consists of an operational amplifier 27, a feedback resistor 30 connected between an output 28 of the operational amplifier 27 and an inverting input 29 of such operational amplifier 27 and an input resistor 31 connected between the inverting input 29 of the operational amplifier 27 and the line node 24. The line node 24 serves as the input of the computation network 26 for a voltage which is to be subtracted. In FIG. 1 the other, non-inverting input of the operational amplifier 27 is connected with the line node or junction 21, which therefore simultaneously serves as the output of the receiver 11 and as the input of the computation network 26 for a voltage which is to be added. In FIG. 2 the non-inverting input of the operational amplifier 27 is connected with the line node or junction 32 which serves as an input of the computation network 26 for a voltage which is to be added. It will be demonstrated in the discussion to follow that a voltage or potential prevails at the line node or junction 32 which is essentially equal to the potential prevailing at the line node 21. In both constructions according to FIGS. 1 and 2 there is formed and amplified the difference of the voltages at the line nodes 21 and 24 by means of the computation network or unit 26, so that at the output 28 of the operational amplifier 27, which also serves as the output of the computation network 26, there appears an output signal which is proportional to the voltage or potential difference between the line nodes 21 and 24, and the proportionality factor is governed by the value of the resistors 30 and 31. This output signal appearing at the output 28 of the computation or arithmetic network 26 delivers the desired measuring pulse, whose further processing has been symbolized by the arrow 33.

It is here to be remarked that the connection of the output 21 of the receiver 11 with the input 24 of the computation network 26 for the voltage which is to be subtracted is accomplished by means of a low-pass filter: the combination of the resistor 23 and the low internal impedance of the reference voltage source 25 namely functions as a RC-low-pass filter which delivers to ground all of the alternating-current voltages which are infed to the line node 24, so that there only appears at the line node 24 the direct-current voltage of the reference voltage source 25.

In FIG. 1 the line node or junction 21 is connected with the control input 10. In this construction the circuit functions in the following manner.

As long as no pulses appear at the output 21 of the receiver 11, then there appears at the control input 10 exactly the reference potential or voltage of the reference voltage source 25, since no current flows through the resistor 23 and therefore there is not present any potential drop. Consequently, the reference potential or voltage forms a control value which is infed to the control input 10. With the already mentioned constant potential difference the potential at the line node 34 follows this control value. The last-mentioned voltage is, however, equal to the difference between the supply voltage of the supply voltage source 7 and the voltage or potential drop at the resistor 8, which, in turn, is proportional to the current of the current supply 6 flowing through the resistor 8. Thus, the current is held at a reference value which linearly corresponds to the control value: in the absence of pulses at the output 21 the current remains constant, and its value is determined by the resistor 8 and the reference and supply voltages. This value of the current is therefore adjustable, for instance, due to the selection of the resistance value of the resistor 8 with given reference and supply voltages.

The switching circuit located between the terminal 4, the output terminal 16, the output terminal 21 and the control input 10, and which is at least approximately closed by means of the field-effect transistor 9 towards the terminal 4, constitutes a basically known regulation circuit which acts upon the current of the current supply 6 in order to maintain constant the voltage or potential at the terminals 4 and 2 in relation to the potential at the terminals 5 and 3, respectively. As already mentioned, this regulation circuit only functions for such changes of the voltage whose frequency spectrum is located above the cut-off frequency. As to this frequency spectrum the current supply functions as the regulated voltage source for the supply of the conductivity cell 1, in that the current is accommodated to the changes of the impedance of the conductivity cell 1 and counteracts such changes by appropriate current changes. In contrast thereto, and as already mentioned, the measuring cell 1 is powered by a current supply functioning as a controlled or regulated current source, in respect of such impedance changes whose frequency spectrum is below the cut-off frequency.

The computation of the current and the action of the regulation circuit will be apparent to the skilled artisan and therefore need not here be further explained. It has been found that the control value which is measurable at the control input 10 is equal to the sum of the reference voltage and the voltage pulse delivered at the output 21 of the receiver 11, and that a linear relationship prevails between the control value and the first time derivative $dR_k/dt$ of the value of the impedance of the measuring cell 1. Additionally, it has been found that the proportionality factor in this linear relationship consists of the product of the value of the resistor 8, the value of the current flowing through the conductivity cell 1 and the value $1/R_k$. Now if, as usual, there can be neglected the changes of the current in relation to the quiescent value I of the current through the particle free measuring cell (whose impedance is equal to $R_k$), then the changes of the control value are proportional to the value $dR_k/R_k$. As already mentioned, these changes of the control value are delivered in the form of measuring pulses by the computation network 26 in that the reference voltage is subtracted from the control value in the computation network 26.

The circuitry of FIG. 1 and the corresponding method practised thereby are advantageously simple. They deliver the desired measuring pulses which are proportional to the value $dR_k/R_k$. What is however disadvantageous is that the potential difference between the line node 34 and the control input 10 at the semiconductor element 9 is incorporated into the computation. This drawback is eliminated by the circuit of FIG. 2 and the corresponding method practiced therewith.

Now in FIG. 2 the line node 21 is connected with the control input 10 by means of a differential amplifier 35. The line node 21 is connected with a non-inverting input 36 of the differential amplifier 35, whereas an output 37 of the differential amplifier 35 is connected with the control input 10. An inverting input 38 of the differential amplifier 35 is connected by means of line node 32 with the line node 34. The non-inverting input of the operational amplifier 27, in contrast to the circuitry of FIG. 1, in the circuit of FIG. 2 is connected with the line node 32. As is known with this type of circuit the differential amplifier 35 operates in such a manner that there is maintained disappearingly small the difference of the voltage or potential between its inputs. The potentials at the line nodes 32 and 21 are thus essentially equal to the control value appearing at the line node 21. The computation network 26 here forms the difference between the actual value and the reference value. By means of the gain or amplification factor of the differential amplifier 35 the operation of the regulation circuit, in comparison to the circuit of FIG. 1, is altered in the manner that the quiescent value I of the current can be regulated much better to be constant. Additionally, there is brought about the beneficial result that now the actual value, instead of the reference value of the current, is processed in the computation network 26, and there is eliminated as an error source the potential drop at the semi-conductor element 9 and the voltage or potential difference between the line node 34 and the control input 10. In comparison to the eliminated error source the new introduced error, caused by the potential difference between both of the inputs of the differential amplifier 35, is negligible.

Since the measuring pulses which are obtained by the circuits of FIGS. 1 and 2 are proportional to the value $dR_k/R_k$, the temperature of the liquid in the conductivity cell 1 does not have any influence upon the measurement result. The temperature also does not have any influence upon the quiescent value I of the current flowing through the measuring cell 1, since this quiescent value I is regulated to be constant. The proportionality actor between the measuring pulses and the values $dR_k/R_k$ contains as the multiplying element the value of the resistor 8 which can be high, without influencing the time-constant of the circuit, as such is the case with the heretofore known circuits. It is for this reason that in comparison to the prior art circuits there is obtained a higher pulse peak and a shorter build-up time upon turning-on the current supply. Finally, the quiescent value I of the current flowing through the measuring cell 1 can be selected to be small, provided this is obtained by a high value of the resistor 8, since in the proportionality factor there is contained the product of the quiescent value divided by the value of the resistor 8, so that such measures do not reduce the pulse peak. On the other hand, it is advantageous that the previously mentioned disturbing side effects are reduced and which are associated with a high quiescent value I.

While there are shown and described present preferred embodiments of the invention, it is to be distinctly understood that the invention is not limited thereto, but may be otherwise variously embodied and practiced within the scope of the following claims.

Accordingly, What I claim is:

1. In a method of producing measuring pulses in a particle analyzer for the analysis of particles suspended in a liquid, especially blood cells, employing a conductivity cell whose impedance between two terminals of the conductivity cell changes upon passage of a particle through the conductivity cell, a controlled-current source for supplying the conductivity cell with a current controlled by a control voltage, and a receiver containing means structured as a high-pass filter and having high input impedance for the essentially currentless removal of a cell voltage between the terminals of the conductivity cell and for generating a received voltage which corresponds to such components of such cell voltage whose frequency is above a cut-off frequency of the high-pass filter, the improvement which comprises the steps of:

generating the control voltage from the sum of a predetermined reference voltage and the received voltage;

generating a measuring signal proportional to the difference of the control voltage and the reference voltage; and the changes as a function of time of the measuring signal constituting the measuring pulses.

2. The method as defined in claim 1, including the steps of:

generating an actual voltage which is essentially equal to the control voltage; and producing the measuring signal from the difference of the actual voltage and the reference voltage.

3. A circuit for producing measuring pulses in a particle analzer for the analysis of particles suspended in a liquid, especially blood cells, comprising:

a conductivity cell having at least two terminals between which there is measured an impedance which varies upon passage of a particle through the conductivity cell;

a controlled-current source having first and second output terminals, each respective one of which is connected with a respective terminal of the conductivity cell, and a control input terminal;

a receiver means comprising an amplifier having high input resistance and a high-pass filter having a given cut-off frequency;

said receiver means having two input terminals, each respective one of which is connected with a respective terminal of the conductivity cell, and an output terminal;

a reference-voltage source having two terminals;

a further amplifier having first and second input terminals and an output terminal;

said controlled-current source comprising a constant-voltage supply, a series resistor and a current-controlling element connected in succession from its first to its second output terminal, the current-controlling element being controlled by means of a control voltage infed to the control input terminal;

said reference-voltage source having one terminal connected with the first terminal of the controlled-current source and the other terminal connected with the second input terminal of the further amplifier;

said controlled-current source having its control input terminal connected by means of a capacitor with the output terminal of the amplifier of the receiver means and by means of a biasing resistor to the second input terminal of the further amplifier; and the measuring pulses appearing at the output terminal of the further amplifier.

4. The circuit as defined in claim 1, wherein:

said further amplifier has its first input terminal connected with the control input terminal of the controlled-current source.

5. The circuit as defined in claim 4, wherein:

said current-controlling element comprises a semiconductor element operated in its saturation region: and said semiconductor element having respective current inflow, current outflow and current control terminals for controlling the inflow-to-outflow current through the semiconductor element by means of a voltage infed to its control terminal.

6. The circuit as defined in claim 3, wherein:

said further amplifier has its first input terminal connected with a circuit node of the controlled-current source defined by the connection of the series resistor with the current-controlling element.

7. The circuit as defined in claim 6, wherein:

said current-controlling element comprises a semiconductor element operated in its saturation region and a differential amplifier having an invering input terminal, a noninverting input terminal and an output terminal;

said semiconductor element having respective current inflow, current outflow and current control terminals for controlling the inflow-to-outflow current through the semiconductor element by means of a voltage infed to its control terminal; and said differential amplifier having its inverting input terminal connected with said circuit node, its noninverting input terminal connected with the control input terminal of the controlled-current source and its output terminal connected with the current control terminal of the semiconductor element.

* * * * *